United States Patent

Nair et al.

Patent Number: 5,470,567
Date of Patent: * Nov. 28, 1995

[54] SYNERGISTIC SKIN DEPIGMENTATION COMPOSITION

[75] Inventors: Xina Nair, E. Amherst; Kenneth M. Tramposch, Williamsville, both of N.Y.

[73] Assignee: Bristol Myers Squibb Company, New York, N.Y.

[*] Notice: The portion of the term of this patent subsequent to Mar. 16, 2020, has been disclaimed.

[21] Appl. No.: 141,503

[22] Filed: Oct. 25, 1993

Related U.S. Application Data

[63] Continuation of Ser. No. 812,600, Dec. 23, 1991, abandoned, which is a continuation-in-part of Ser. No. 554,904, Jul. 24, 1990, Pat. No. 5,194,247, which is a continuation-in-part of Ser. No. 397,921, Aug. 24, 1989, abandoned.

[51] Int. Cl.$^6$ .................................... A61K 31/07
[52] U.S. Cl. .............................. 424/59; 424/62; 424/401; 514/725; 514/844
[58] Field of Search ............................. 424/401, 59, 62; 514/859, 844, 725

[56] References Cited

U.S. PATENT DOCUMENTS

| | | | |
|---|---|---|---|
| 3,856,934 | 12/1974 | Kligman | 424/62 |
| 4,214,000 | 7/1980 | Papa | 514/784 |
| 4,247,547 | 1/1981 | Marks | 424/78.05 |
| 4,608,392 | 8/1986 | Jacquet et al. | 424/63 |
| 4,678,663 | 7/1987 | Scott et al. | 424/62 |
| 4,727,088 | 2/1988 | Scott et al. | 514/725 |
| 4,857,525 | 8/1989 | Philippe et al. | 514/227.5 |
| 5,034,228 | 7/1991 | Maybeck et al. | 424/401 |
| 5,093,360 | 3/1992 | Yu et al. | 514/859 |

FOREIGN PATENT DOCUMENTS 982945  2/1976  Canada.

*Primary Examiner*—Melvyn I. Marquis
*Assistant Examiner*—Amy Hulina
*Attorney, Agent, or Firm*—Anthony M. Santini; Morton S. Simon

[57] ABSTRACT

There is disclosed a synergistic composition and process for skin depigmentation with reduced irritation which does not employ a corticosteroid and which employs a substituted oxybenzene and a retinoid.

8 Claims, 5 Drawing Sheets

SUMMATION OF DRAIZE SCORES FOR ERYTHEMA, EDEMA AND SCALING.
1= MINIMUM EFFECT, 2= SLIGHT EFFECT, 3= MODERATE TO SEVERE EFFECT
AND 4= SEVERE EFFECT. THE MAXIMUM ATTAINABLE SCORE = 12.

SYNERGISTIC SKIN DEPIGMENTATION COMPOSITION

CROSS-REFERENCE TO RELATED APPLICATIONS

This application is a continuation of application Ser. No. 07/812,600, filed Dec. 23, 1991, now abandoned, which is, in turn a continuation-in-part of application Ser. No. 07/554,904, filed Jul. 24, 1990, now U.S. Pat. No. 5,194,247, issued Mar. 16, 1993. Application Ser. No. 07/554,904 is a continuation-in-part of application Ser. No. 07/397,921 filed Aug. 24, 1989 and now abandoned.

BACKGROUND OF THE INVENTION

This invention relates to a steroid-free synergistic skin depigmentation composition comprising a substituted oxybenzene and a retinoid.

Substituted oxybenzenes (or substituted phenols), such as 4-hydroxyanisole, are present as the active ingredient in products used topically for depigmenting or lightening skin. These products are used in the treatment of hyperpigmentation of skin associated with various skin disorders or diseases. The hyperpigmentation is generally the result of increased melanin deposition in epidermal cells. Hyperpigmentation of skin is associated with freckles, senile lentigo, lentigines, melasma, post-inflammatory hyperpigmentation, sunburn, phototoxic reactions and other conditions. In general, these cases of hyperpigmentation are not life-threatening, but are viewed as cosmetically undesirable and psychologically debilitating.

Local side effects are often associated with the existing products containing more than 2% hydroquinone or 4-hydroxyanisole. These side effects include localized irritation and irreversible depigmentation. Products containing 2% or less of hydroquinone or 4-hydroxyanisole are generally regarded as ineffective in the treatment of lentigo or melasma.

All-trans retinoic acid (vitamin A acid) applied topically has been reported to lighten the color of lentigo in humans. All-trans retinoic acid is known to increase epidermal cell turnover in normal skin and suppress epidermal cell turnover under stimulated or hyperproliferative conditions. It causes epidermal keratinization and decreases the number of normal cell layers of the stratum corneum. This decrease in thickness of the barrier may potentiate the penetration of other topical agents.

U.S. Pat. No. 3,856,934 and Canadian Patent No. 982,945 disclose a synergistic composition for depigmentation of skin comprising a mixture of hydroquinone, retinoic acid, and a corticosteroid. The U.S. patent also discloses that the double combination of hydroquinone and retinoic acid was not synergistic. Therefore, all three components were needed for the synergistic activity.

The Canadian patent discloses that hydroquinone monomethyl ether (4-hydroxyanisole) may be used in the composition instead of hydroquinone.

In these patents the corticosteroid is regarded as necessary to bring irritation down to acceptable levels. However, the use of a corticosteroid possesses some disadvantages, i.e., it can be dangerous to use in intertriginous regions, and it may cause skin atrophy, rebound phenomenon and telangiectasia.

BRIEF DESCRIPTION OF THE INVENTION

It has now been discovered that the combination of a substituted oxybenzene and a retinoid—without the presence of a corticosteroid—results in synergistic depigmentation with diminished irritation of the skin when applied topically in a pharmaceutically acceptable topical vehicle. For example, the combination of 1% by weight of 4-hydroxyanisole and 0.01% by weight of all-trans retinoic acid produced depigmentation of skin that was equivalent to the effect produced by 5% by weight of 4-hydroxyanisole.

Individually, 4-hydroxyanisole (1% by weight) and all-trans retinoic acid (0.01% by weight) are without any significant depigmenting activity. 4-Hydroxyanisole alone at 5% by weight caused depigmentation that was slower to reverse in Yucatan minipigs.

The depigmentation produced by the combination of 1% by weight of 4-hydroxyanisole with 0.01% by weight of all-trans retinoic acid showed little or no local irritation, and the depigmentation was reversible in 6–7 weeks after stopping the treatment.

DETAILED DESCRIPTION OF THE INVENTION

Figure 1:
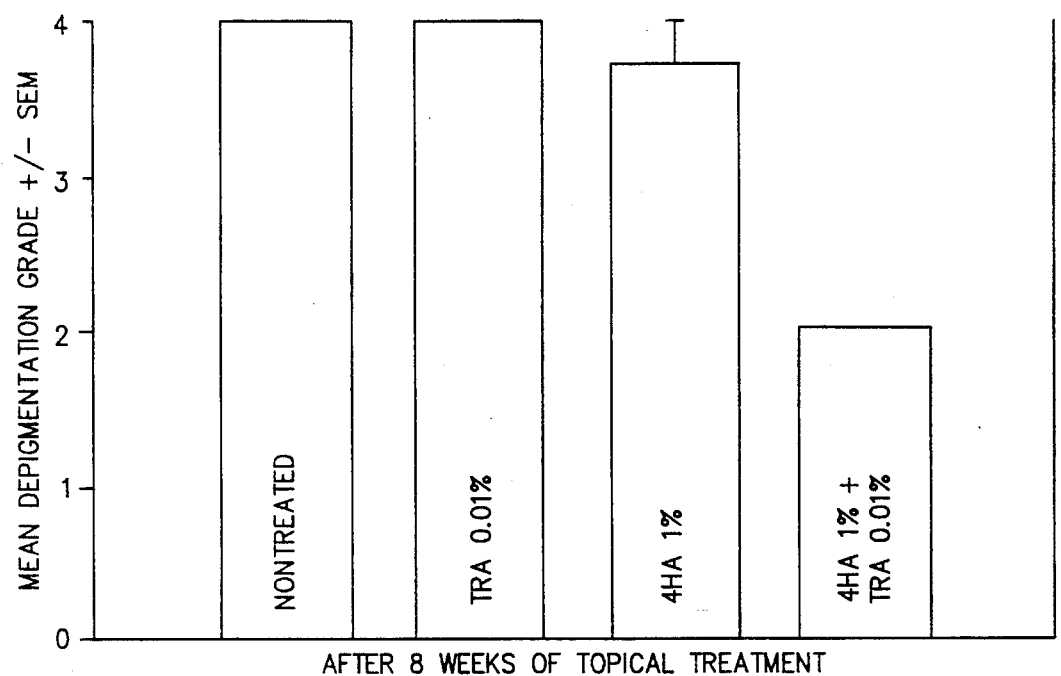
FIGS. 1 and 8 show the synergistic interaction of all-trans retinoic acid and 4-hydroxyanisole.

In one aspect of the present invention, there is provided a synergistic composition for skin depigmentation, which does not contain a corticosteroid, comprising a substituted oxybenzene and a retinoid. Exemplary oxybenzene derivatives are 4-hydroxyanisole, hydroquinone monoesters, 5-hydroxybenzofuran and the like.

Exemplary retinoids include all-trans retinoic acid, 11-cis, 13-cis-12-hydroxymethyl retinoic acid δ-lactone, (N-acetyl-4-aminophenyl) retinoate and the like. A pharmaceutically acceptable topical vehicle is used with the substituted oxybenzene/retinoid combinations.

In another aspect, the present invention relates to a method for skin depigmentation comprising topically applying to the skin a combination of a substituted oxybenzene and a retinoid. Exemplary substituted oxybenzenes and include those referred to above. The combination is used in a pharmaceutically acceptable topical vehicle.

A pharmaceutically acceptable topical vehicle into which the substituted oxybenzene and retinoid are incorporated may be a cream, gel, ointment, powder, aerosol, emulsion or solution suitable for topical administration. Such topical vehicles are well-known in the art as exemplified by U.S. Pat. No. 4,185,100, the disclosure of which is incorporated herein by reference.

Preferably, the composition of this invention will contain from about 0.1% by weight to about 5% by weight of substituted oxybenzene and from about 0.001% by weight to about 1% by weight of one or more suitable retinoid compound(s).

Particularly preferred compositions comprise from about 1% by weight to about 2% by weight of substituted oxybenzene compound, such as 4-hydroxyanisole and from about 0.01% by weight to about 0.1% by weight of a retinoid, such as all-trans retinoic acid; 11-cis,13-cis-12-hydroxymethyl retinoic acid δ-lactone or (N-acetyl-4-amino-phenyl) retinoate.

Useful substituted oxybenzene are those conforming to either formula I or II. Formula I is

(I)

wherein R' is $C_{1-3}$ alkyl or C(0)R" and R"=$C_{1-6}$ alkyl or $C_{6-20}$ aryl.

Formula II is:

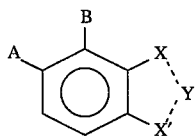

(II)

wherein one of A or B is OH and the other is H; X and X' may each independently be C, N, O or S, with X and X' being linked via a Y bridge (the dotted lines indicate that the linkages between X or X' and Y may be single or double bonds); Y may be —$CH_2$—, =CH—, C(0)—, —CH=CH—, or —$CH_2$—C(0)—.

Useful retinoids include a large number of compounds.

The compound (N-acetyl-4-aminophenyl) retinoate has the formula:

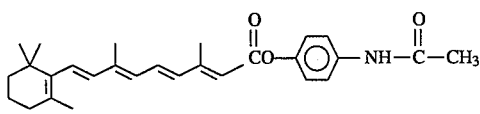

and the compound 11-cis,13-cis-12-hydroxymethyl retinoic acid δ-lactone has the formula:

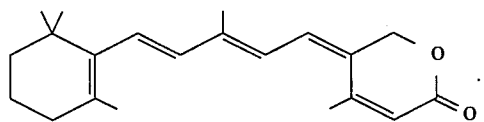

Other useful retinoids include those referred to in the table and in the following paragraphs.

TABLE: CHEMICAL, COMMON AND/OR COMMERCIAL NAME OF RETINOID

Isotretinoin
13-cis-retinoic acid
ACCUTANE
Etretinate
TEGISON
(all-E)-9-(4-methoxy-2,3,6-trimethylphenyl)-3,7-dimethyl-2,4,6,8-nonatetraenoic acid ethyl ester
Etretin
(all-E)-9-(4-methoxy-2,3,6,-trimethylphenyl)-3,7-dimethyl-3,4,6,8, nonatetraenoic acid
Motretinide
N-ethyl-9-(4-methoxy-2,3,6-trimethylphenyl)-3,7-dimethyl- 2,4,6,8-nonatetraenamide
(E,E)-9-(2,6-dichloro-4-methoxy-3-methylphenyl)-3,7-dimethyl- 2,4,6,8-nonatetraenoic acid ethyl ester
7,8-didehydroretinoic acid
(E,E)-4-[2-methyl-4-(2,6,6-trimethyl-1-cyclohexene-1-yl)-1,3-butadienyl]benzoic acid
(E,E)-4-methyl-6-(2,6,6-trimethyl-1-cyclohexen-1-Yl-)-1,3,5-hexatrienyl]benzoic acid
(all-E)-3,7-dimethyl-9-(3-thienyl)-2,4,6,8-nonatetraenoic acid
(E,E,E)-3-methyl-7-(5,6,7,8-tetrahydro-5,5,8-tetramethyl-2-naphthlenyl)-2,4,6-octatrienoic acid
(E)-6-[2-(2,6,6-trimethyl-1-cyclohexen-1-yl)ethenyl)]-2-naphthalenecarboxylic acid
(E,E,E)-7-(2,3-dihydro-1,1,3,3,-tetramethyl-1H-inden-5-yl)-3-methyl-2,4,6-octatrienoic acid
(E)-4-(2,3-dihydro-1,1,3,3-tetramethyl-1H-inden-5-yl)-1-propenyl]benzoic acid
TTNPB
(E)-4-[2-(5,6,7,8-tetrahydro-5,5,8,8-tetramethyl-2-naphthalenyl- 1-propenyl]benzoic acid
(E)-4-[2-(5,6,7,8-tetrahydro-3-methyl-5,5,8,8-tetramethyl-2-naphthalenyl-1-propenyl] benzoic acid
(E)-1,2,3,4-tetrahydro-1,1,4,4-tetramethyl-6-(1-methyl-2-phenylethenyl)naphthalene
6-(1,2,3,4-tetrahydro-1,1,4,4-tetramethyl-6-naphthyl)-2-naphthalene-carboxylic acid
(E)-6-[2-[4-(ethylsulfonyl)phenyl-1-methylethenyl]- 1,2,3,4-tetrahydro-1,1,4,4-tetramethylnaphthalene
4-[(5,6,7,8-tetrahydro-5,5,8,8-tetramethyl-2-naphthalenyl)ethynyl]benzoic acid
(E)-2-(1,1,4,4-tetramethyl-1,2,3,4-tetrahydronaphth-7-yl-[4-tetrazol-5-yl)phenyl]-1-propene
(E)-4-[2-(5,6,7,8-tetrahydro-7-hydroxy-5,5,8,8-tetramethyl-2-naphthaleny)-1-propenyl]benzyl alcohol
AM-80
2-(4-Carboxybenzamido)-5,6,7,8-tetrahydro-5,5,8,8-tetramethylnaphthalene
AM-580
2-[N-(4-Carboxyphenyl)carbamoyl]-5,6,7,8-tetrahydro- 5,5,8,8-tetramethyl-naphthalene
CH-55
1-[3,5-(Di-tert-butyl)benzoyl]-2-(4-Carboxyphenyl)-ethene
CD-271
6-[4-Methoxy-3-tricycle(3.3.1.1.)dec-1-ylphenyl]-2-naphthalene carboxylic acid.
TTNT
2-(5,6,7,8-tetrahydro-5,5,8,8-tetramethyl-2-naphthyl)-6-benzo(b) thiophene carboxylic acid
TTNF
2-(5,6,7,8-tetrahydro-5,5,8,8-tetramethyl-2-naphthyl)-6-benzo(b) furancarboxylic acid
TTNN
2-(5,6,7,8-tetrahydro-5,5,8,8-tetramethyl-2-naphthyl)-6-naphthalene carboxylic acid
p-(5,6,7,8-tetrahydro-5,5,8,8-tetramethyl-2-anthracenyl)benzoic acid Esters or amides of 13-trans retinoic acid or 13-cis retinoic acid wherein the —OH group of the carboxylic acid (—COOH) group is substituted by —$OR^1$ or —$NR^2R^3$, wherein $R^1$, $R^2$ and $R^3$ are such that these esters or amides can be converted to 13-trans retinoic acid or 13-cis retinoic acid through hydrolysis, metabolism, cleavage, etc. Retinoic acid, including all-trans retinoic acid 3,7-dimethyl-9-(2,6,6-trimethyl-1-cyclohexen-1-yl)- 2,4,6, 8-nonatetraenal (ie., Vitamin A aldehyde).

Included in the term "retinoid" are pharmaceutically acceptable geometric and stereoisomers of these compounds and their analogs. In addition "retinoid" is intended to include all pharmaceutically acceptable derivatives, for example, polyene derivatives such as the phenolic esters of polyolefinic carboxylic acids derived from retinoids or chemical intermediates therefor. The derivatives disclosed in U.S. Pat. No. 4,595,696 are useful herein.

One group of preferred retinoids are compounds of Formula III:

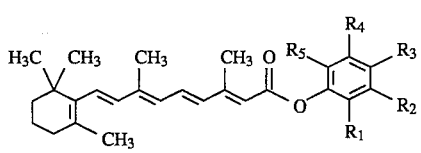

wherein $R_1$, $R_2$, $R_3$, $R_4$ and $R_5$ are independently selected from the group consisting of H, Cl, $OR_6$, straight or branched alkyl of 1 to 10 carbon atoms, $NO_2$, $COOR_6$, CN, $OR_6$, $NR_6R_7$, $NR_6C(=S)NR_7R_8$, $NR_6COR_7$, $SO_2NR_6R_7$, $CH(CH_3)COOH$, $CONR_6R_7$, $COR_6$, $OCONR_6R_7$, $NR_6COONR_7$, $R_9OR_6$, $NR_6SO_2R_7$, $Si(CH_3)_3$, and $NR_6CONR_7R_8$, $R_3$ together with $R_4$ forms a benzo ring, or taken together with $R_2$ forms a benzo or tetrahydrobenzo ring, or together with $R_2$ and $R_1$ forms a:

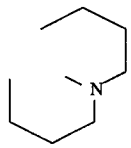

moiety, or together with $R_2$, forms a

moiety or $R_2$ together with $R_1$ forms a benzo ring, or $R_2$ together with $R_3$ forms a

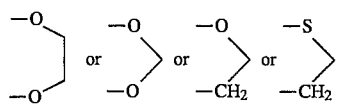

moiety, or $R_1$ is independently selected from the group consisting of

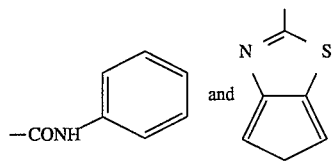

moieties, $R_6$, $R_7$ and $R_8$ are independently selected from the group consisting of straight or branched alkyl containing from 1 to 10 carbon atoms, aryl containing from 6 to 10 carbon atoms and hydrogen, and $R_9$ is alkylene of 1 to 6 carbon atoms and iron carbonyl complexes thereof. $NR_6COR_7$, $CONR_6R_7$, $SO_2NR_6R_7$, $OCONR_6R_7$, $NR_6COOR_7$, $NR_6CONR_7R_8$, $NR_6SO_2R_7$ and $NR_6C(=S)NR_7R_8$ are preferred. Also preferred are compounds of this formula wherein $R_3$ is $NHCOCH_3$ and $R_1$, $R_2$ and $R_4$ are H.

Compounds within this preferred group are disclosed in International Publication Numbers WO91/01128 and WO91/01301, both published on Feb. 7, 1991.

IN VIVO EXPERIMENTS

A. Normal Depigmenting Activity

Healthy, female Yucatan minipigs weighing from 25–40 kgms were used in these studies. The animals were selected for even tan to brown skin color. These animals were housed individually in standard stainless steel pens in temperature and humidity controlled rooms with 12-hour cycled lighting. Food was provided at specified times and water was available ad libitum.

Test materials were prepared as solutions in a PEG8/ ethanol vehicle comprising 5 parts by weight of PEG8 (polyethylene glycol 400, a polymer of ethylene oxide that conforms generally to the formula $H(OCH_2CH_2)_nOH$, wherein n has an average value of 8) and 95 parts by weight of ethanol. Test solutions (25 µl) were applied twice daily to a 12.5 $cm^2$ area of the flank skin five days a week for 8–12 weeks. Test sites were graded at weekly intervals for signs of local irritation and changes in depigmentation using the following grading system:
 1= Complete depigmentation
 2= Definite uniform depigmentation of test site
 3= Small spots of depigmentation
 4= Same color as the normal skin
At the end of 8–12 weeks of treatment, selected test sites were biopsied and skin specimens were processed for microscopic examination. The remaining sites were observed for the next 7 weeks for repigmentation or reversibility of depigmentation.

The results of 1% by weight of 4-hydroxyanisole (4HA) combined with 0.01% of all-trans retinoic acid (TRA) are shown in FIG. 1. 4-Hydroxyanisole combined with all-trans retinoic acid showed moderate depigmentation during 6–12 weeks of treatment. Under the same conditions, 4-hydroxyanisole or all-trans retinoic acid alone produced slight to no effect.

Figure 2:
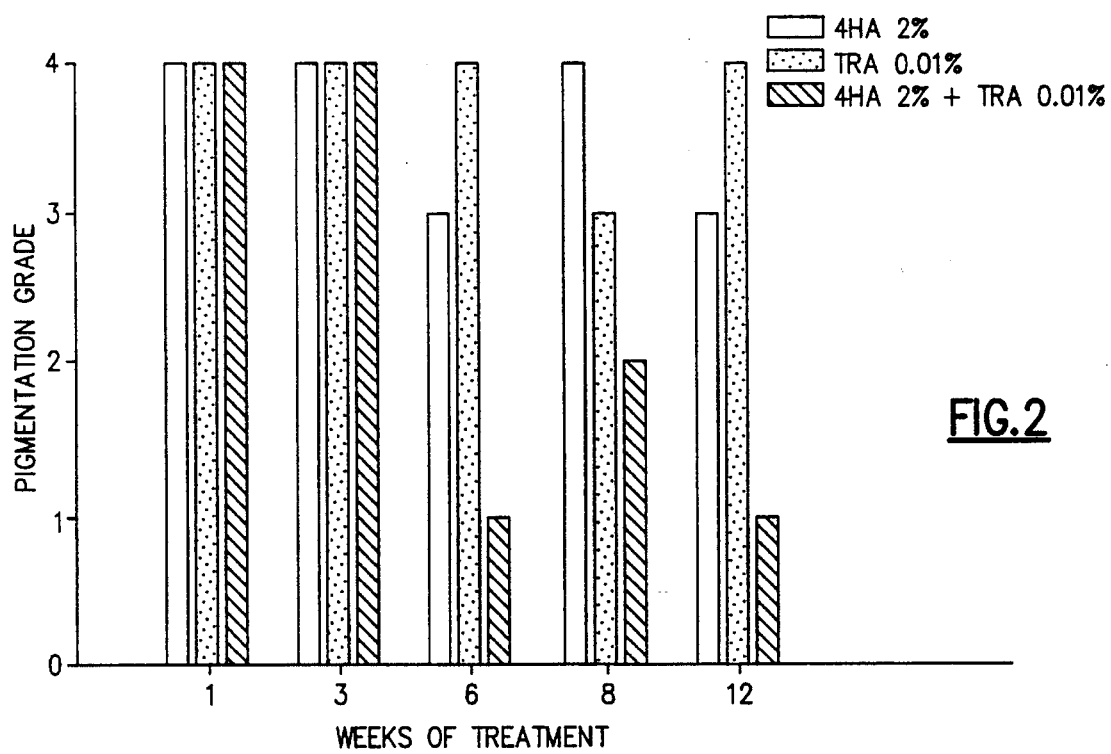
FIG. 2 shows the synergistic interaction of all-trans retinoic acid and 4-hydroxyanisole over a 12 week period.

FIG. 2 shows that 2% by weight of 4-hydroxyanisole combined with 0.01% by weight of all-trans retinoic acid showed an earlier onset of depigmentation than 4-hydroxyanisole or all-trans retinoic acid alone.

Figure 3:
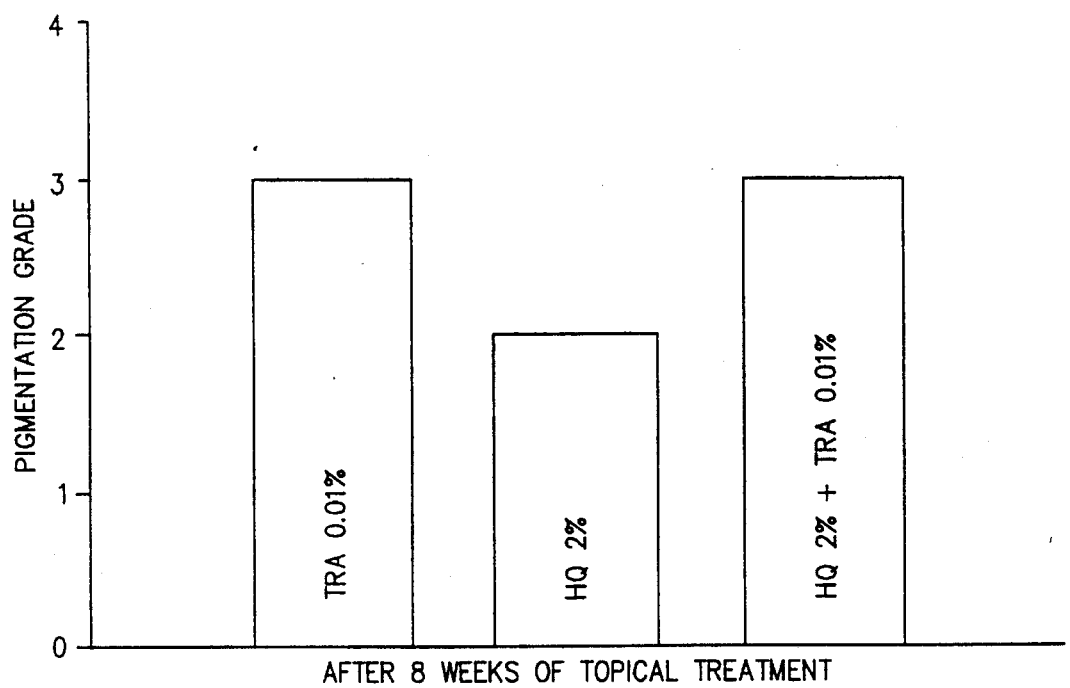
FIG. 3 shows the lack of synergism of a composition containing all-trans retinoic acid and hydroquinone.

In contrast to the combination of 4-hydroxyanisole and all-trans retinoic acid, 2% by weight of hydroquinone (HQ)

combined with 0.01% all-trans retinoic acid was only slightly active and more irritating after eight weeks of treatment, whereas hydroquinone alone was moderately active and all-trans retinoic acid alone was inactive, see FIG. 3. The lower activity with the hydroquinone and all-trans retinoic acid combination is reflective of an increase in pigmentation noted on sites exposed to all-trans retinoic acid. This may be caused by the increased irritation caused by all-trans retinoic acid and hydroquinone.

Figure 4:
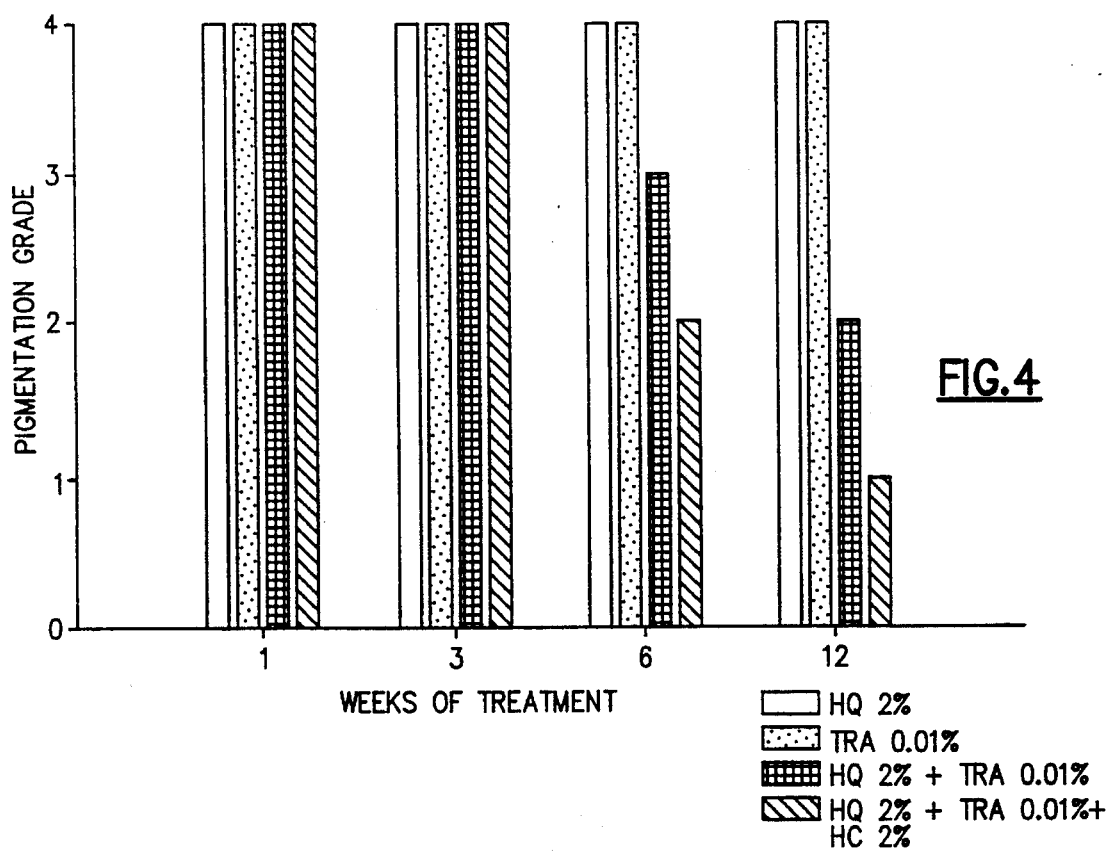
FIGS. 4 and 5 show the results of various combinations of ingredients.

FIG. 4 shows that 2% by weight of hydroquinone combined with 0.01% by weight of all-trans retinoic acid and 2% by weight of hydrocortisone was comparatively more active than 2% by weight of hydroquinone or 0.01% by weight of all-trans retinoic acid each alone, or a combination of 2% by weight of hydroquinone and 0.01% by weight of all-trans retinoic acid. Hydroquinone combined with all-trans retinoic acid was, in general, less effective than the combination of 4-hydroxyanisole and all-trans retinoic acid.

Figure 5:
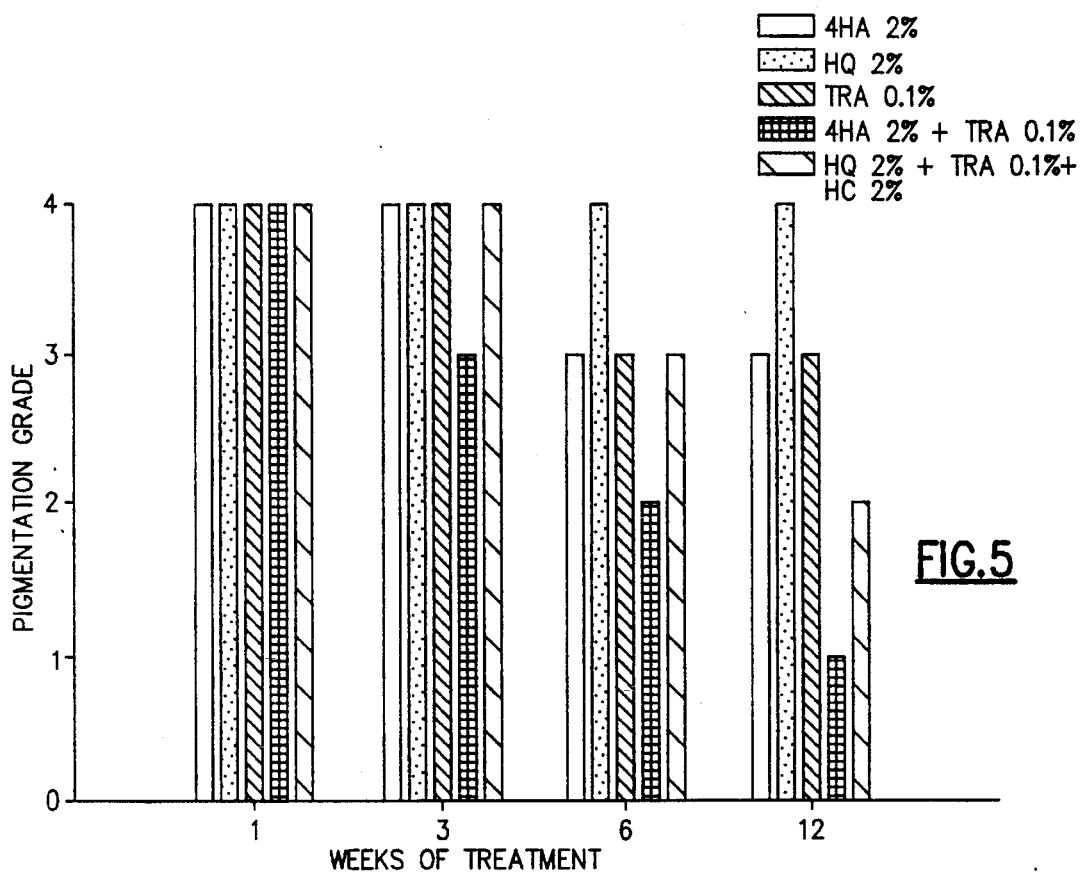

FIG. 5 shows that 2% by weight of hydroquinone combined with 0.1% by weight of all-trans retinoic acid and 2% by weight of hydrocortisone was less effective than the combination of 2% by weight of 4-hydroxyanisole with 0.1% by weight of all-trans retinoic acid.

Figure 6:
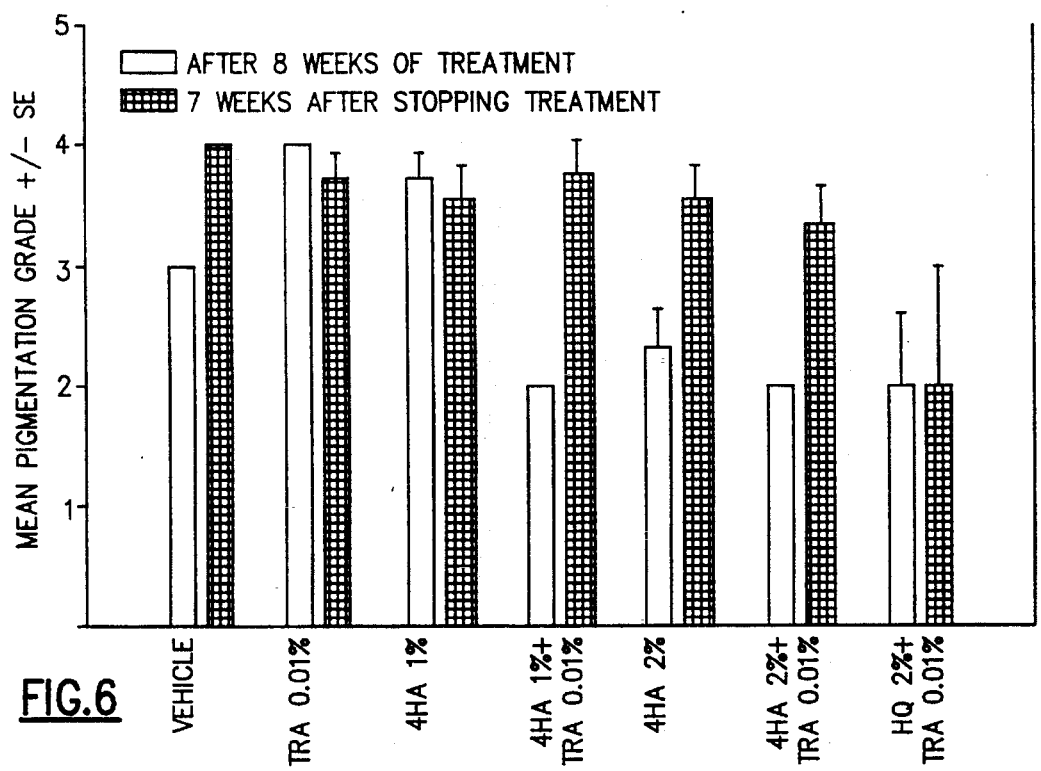
FIG. 6 shows the reversibility of depigmentation of various compositions.

The results shown in FIG. 6 again show that the combinations of 1% by weight of 4-hydroxyanisole with 0.01% all-trans retinoic acid applied for eight weeks is active, whereas 1% by weight of 4-hydroxyanisole or 0.01% all-trans retinoic acid alone have little or no activity. These results also show that the moderate depigmentation produced by the combination of 2% by weight or 1% by weight of 4-hydroxyanisole with 0.01% by weight of all-trans retinoic acid is reversible and returns to near normal color within seven weeks after discontinuing the treatment. On the other hand, 2% by weight of hydroquinone plus 0.01% by weight of all-trans retinoic acid, which showed moderate activity after eight weeks of application, failed to show any significant degree of reversibility of the depigmentation during the same time period. It is desirable to have reversible rather than permanent depigmentation since permanent depigmentation results in an unsightly area of light skin which does not recover its normal pigmentation.

B. Local Irritation

Local irritation was assessed on pig skin during the course of daily topical application of the respective agents. Comparison of the local skin irritation potential of 4-hydroxyanisole and hydroquinone with and without all-trans retinoic acid is based on the summation of Draize scores for erythema, edema and scaling. 1= minimum effect, 2= slight effect, 3= moderate to severe effect, and 4= severe effect. The maximum attainable score= 12. Results are given in Table 1 and FIG. 7.

TABLE 1

Comparison of Local Skin Irritation potential of 4-Hydroxyanisole and Hydroquinone Based on the Summation of Draize Scores for Erythema, Edema and Scaling of Skin

| Treatment | Skin Irritation | | |
|---|---|---|---|
| | WK 1 | WK 3 | WK 6 |
| 2% by weight 4-hydroxyanisole | 3 | 0 | 0 |
| 2% by weight hydroquinone | 3 | 6 | 4 |
| 0.01% by weight all-trans retinoic acid | 3 | 0 | 2 |
| 2% by weight 4-hydroxyanisole + 0.01% by weight all-trans retinoic acid | 3 | 0 | 1 |
| 2% by weight hydroquinone + 0.01% by weight all-trans retinoic acid | 3 | 6 | 3 |

It will be seen from Table 1 that 4-hydroxyanisole with and without all-trans retinoic acid elicited less irritation than hydroquinone with and without all-trans retinoic acid. Hydroquinone combined with all-trans retinoic acid and hydrocortisone was generally more irritating than hydroquinone combined with all-trans retinoic acid. It is speculated that the vasoconstrictor action of hydrocortisone causes the longer retention of hydroquinone and all-trans retinoic acid locally, leading to greater irritation.

Hence, 4-hydroxyanisole combined with all-trans retinoic acid showed less irritation and a synergistic depigmenting activity, whereas hydroquinone combined with all-trans retinoic acid was more irritating and showed similar or lower activity than hydroquinone alone. These results show that the combination of low concentrations of 4-hydroxyanisole and all-trans retinoic acid without hydrocortisone unexpectedly produce effective depigmentation with lower irritation and improved potential for inducing reversible skin depigmentation.

Figure 7:
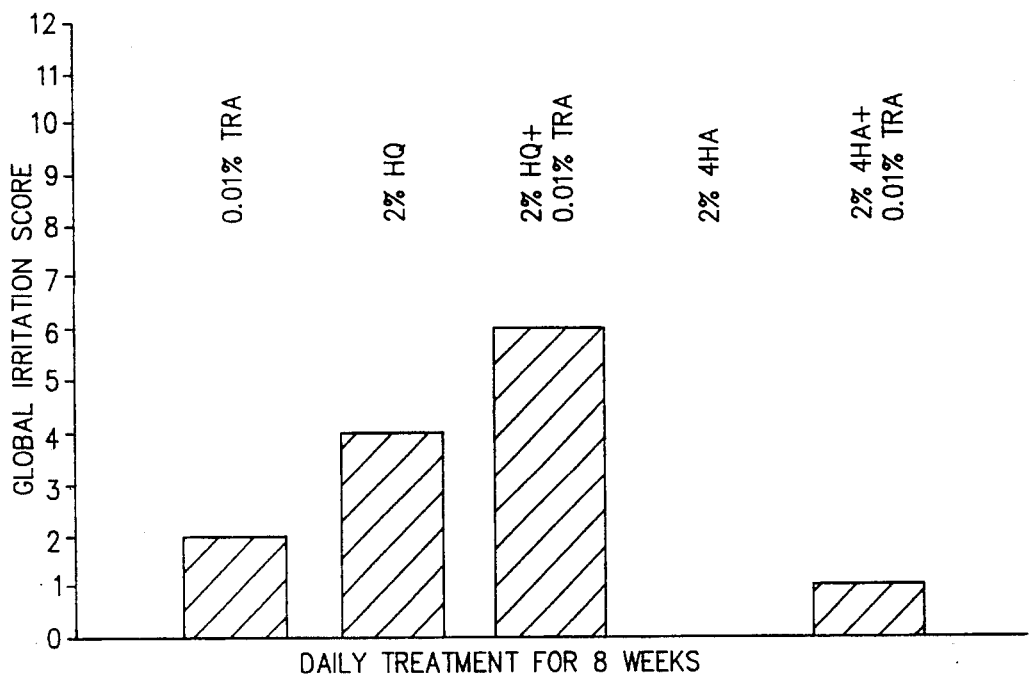
FIG. 7 shows the irritation effects of various combinations.

FIG. 7 shows that the greater depigmentation noted with 2% by weight of 4-hydroxyanisole combined with the low dose of 0.01% by weight of all-trans retinoic acid was associated with less local irritation compared to the combination of 2% by weight of hydroquinone and 0.01% by weight of all-trans retinoic acid.

In general, hydroquinone alone or combined with all-trans retinoic acid and/or hydrocortisone was more locally irritating than similar concentrations of 4-hydroxyanisole alone or combined with all-trans retinoic acid.

C. Depigmentation Activity on UVR-induced Hyperpigmentation

Exposure of human skin to ultraviolet radiation (UVR) leads to the appearance of erythema and hyperpigmentation (tanning). In a similar manner, exposure of Yucatan minipig skin to UVR also elicits erythema followed by hyperpigmentation. The Yucatan pig skin shares many physiologic and morphologic characteristics with human skin. The thickness and general morphology of epidermis and dermis, tritiated thymidine labeling pattern and index of epidermal cells, epidermal cell turnover time and size, orientation, and distribution of vessels in skin are similar to that in humans. In view of the similarity of the pig skin to human skin, the Yucatan pig was used as a model for screening depigmenting activity on UVR induced hyperpigmentation of various compounds.

Lentigo is localized skin hyperpigmentation which is characterized by a basal melanin synthesis rate and an increased number of melanocytes at the basal level. In the treatment of solar lentigo, it is desirable to only depigment the elevated or locally stimulated hyperpigmentation and not affect normally pigmented skin around the lesion.

In the following studies, Yucatan pigs were exposed to UVR to induce hyperpigmentation. The test materials were prepared as solutions in a PEG8/ethanol vehicle comprising five parts by weight of PEG8 and 95 parts by weight of ethanol. Test solutions were applied twice daily at a dose of 2 µl/cm² of the flank skin. Test sites were graded on a scale of 0–4, with 4 being the maximum degree of induced hyperpigmentation and 0 representing complete depigmentation of the induced hyperpigmentation, i.e., back to the color of the normal skin.

Figure 8:
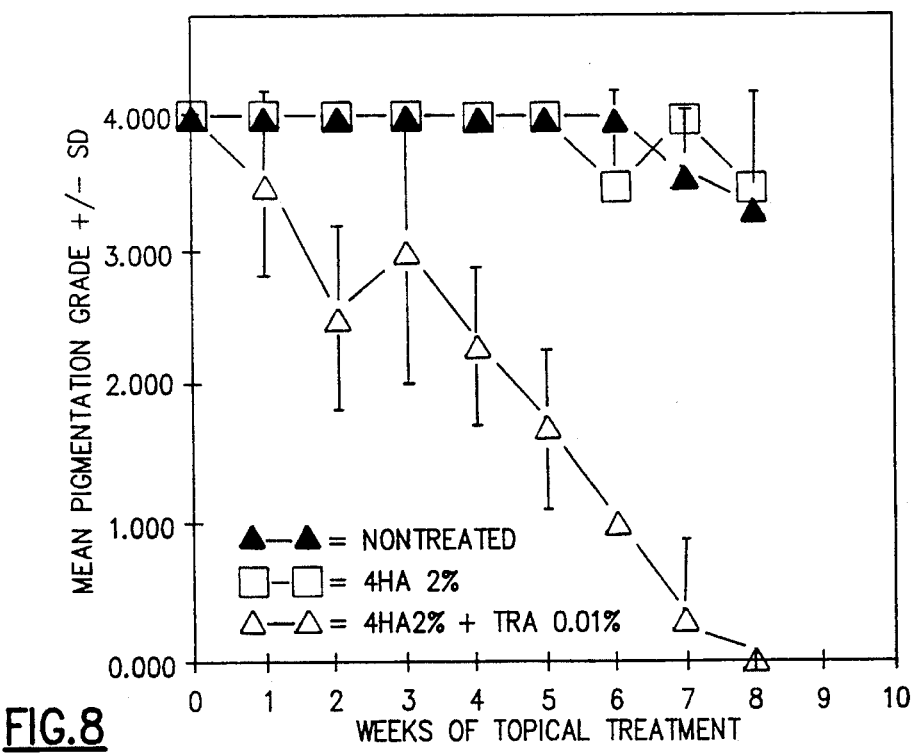

As shown in FIG. 8, 2% by weight of 4HA combined with 0.01% by weight of TRA is significantly more active than 2% by weight of 4HA by itself and produced complete depigmentation of the UVR-induced hyperpigmented spot within eight weeks of treatment. Additionally, the depigmentation of the induced pigmentation by the combination of 4HA and TRA was apparent after the first week of treatment.

Figure 9:
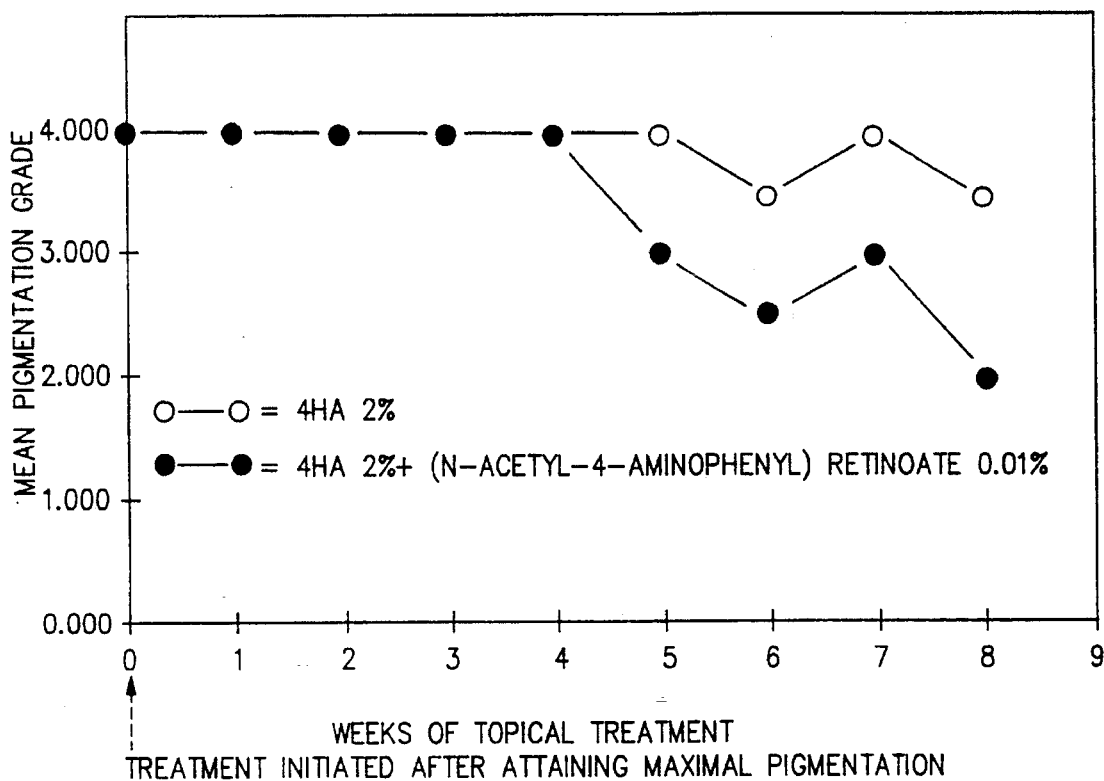
FIG. 9 shows the interaction of (N-acetyl-4-amino-phenyl) retinoate and 4-hydroxyanisole.

FIG. 9 shows that 2% by weight of 4HA combined with 0.01% by weight of the retinoid (N-acetyl-4-aminophenyl) retinoate is more active than 2% by weight of 4HA by itself.

Figure 10:
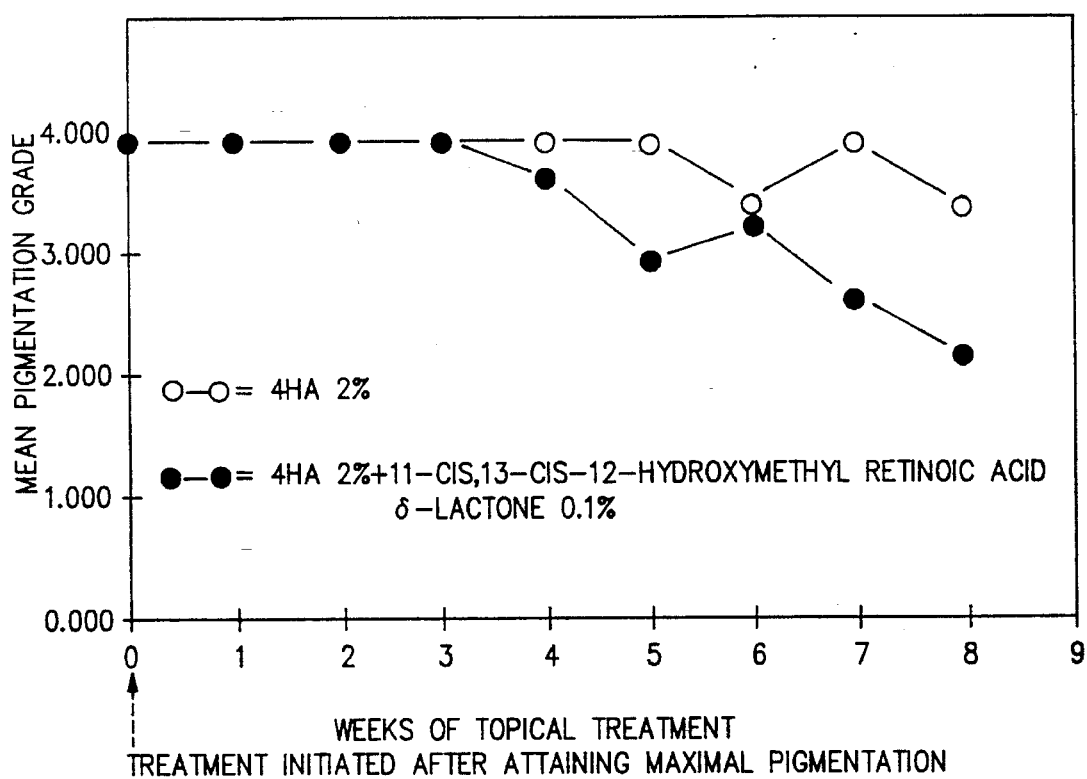
FIG. 10 shows the interaction of all-trans 11-cis, 13-cis-12-hydroxymethyl retinoic acid δ-lactone and 4-hydroxyanisole.

FIG. 10 shows that 2% by weight of 4HA combined with 0.1% by weight of the retinoid 11-cis-13-cis-12-hydroxymethyl retinoic acid δ-lactone is more active than 2% by weight of 4HA by itself.

Reasonable variations, such as those which would occur to a skilled artisan, can be made herein without departing from the scope of the invention.

What is claimed is:

1. A synergistic composition for skin depigmentation free of corticosteroid comprising:
    (a) 4-hydroxyanisole in an amount from about 0.1% to about 2% by weight;
    (b) a retinoid selected from the group consisting of all-trans retinoic acid in an amount from about 0.001% to about 0.1% by weight, (N-acetyl-4-aminophenyl) retinoate in an amount from about 0.001% to about 0.01%, and 11-cis, 13-cis-12 -hydroxymethyl retinoic acid δ-lactone in an amount from about 0.001% to about 0.1% by weight; and
    (c) a dermatologically acceptable carrier.

2. The composition of claim 1 comprising from about 1% to about 2% of 4-hydroxyanisole and from about 0.01% to about 0.1% of all-trans retinoic acid.

3. The composition of claim 1 comprising from about 1% to about 2% of 4-hydroxyanisole and from about 0.001% to about 0.01% of (N-acetyl-4-aminophenyl) retinoate.

4. The composition of claim 1 comprising from about 1% to about 2% of 4-hydroxyanisole and from about 0.01% to about 0.1% of 11-cis, 13-cis-12-hydroxymethyl retinoic acid δ-lactone.

5. A method for skin depigmentation which comprises topically applying to the skin a synergistic composition free of corticosteroid which comprises:
    (a) 4-hydroxyanisole in an amount from about 0.1% to about 2% by weight;
    (b) a retinoid selected from the group consisting of all-trans retinoic acid in an amount from about 0.001% to about 0.1% by weight, (N-acetyl-4-amino-phenyl) retinoate in an amount from about 0.001% to about 0.01% by weight and 11-cis, 13-cis-12-hydroxymethyl retinoic acid δ-lactone in an amount from about 0.001% to about 0.1% by weight; and
    (c) a dermatologically acceptable carrier.

6. The method of claim 5 wherein the composition comprises from about 1% to about 2% of 4-hydroxyanisole and from about 0.01% to about 0.1% of all-trans retinoic acid.

7. The method of claim 5 wherein the composition comprises from about 1% to about 2% of 4-hydroxyanisole and from about 0.001% to about 0.01% of (N-acetyl-4-aminophenyl) retinoate.

8. The method of claim 5 wherein the composition comprises from about 1% to about 2% of 4-hydroxyanisole and from about 0.01% to about 0.1% of 11-cis, 13-cis-12-hydroxymethyl retinoic acid δ-lactone.

* * * * *